(12) United States Patent
Grant et al.

(10) Patent No.: US 11,118,172 B2
(45) Date of Patent: *Sep. 14, 2021

(54) SYSTEM AND METHOD FOR USING ELECTROMAGNETIC RADIATION TO INFLUENCE CELLULAR STRUCTURES

(71) Applicant: STRATHSPEY CROWN HOLDINGS, LLC, Newport Beach, CA (US)

(72) Inventors: Robert Edward Grant, Laguna Beach, CA (US); Todd Mirzai, Honolulu, HI (US); Matthew T. Case, Laguna Hills, CA (US)

(73) Assignee: STRATHSPEY CROWN HOLDINGS, LLC, Newport Beach, CA (US)

(*) Notice: Subject to any disclaimer, the term of this patent is extended or adjusted under 35 U.S.C. 154(b) by 1460 days.

This patent is subject to a terminal disclaimer.

(21) Appl. No.: 14/632,941

(22) Filed: Feb. 26, 2015

(65) Prior Publication Data

US 2016/0074669 A1   Mar. 17, 2016

Related U.S. Application Data

(63) Continuation-in-part of application No. 14/488,101, filed on Sep. 16, 2014.

(51) Int. Cl.
*C12N 13/00* (2006.01)
*A61N 5/00* (2006.01)
(Continued)

(52) U.S. Cl.
CPC ............ *C12N 13/00* (2013.01); *A61B 5/0036* (2018.08); *A61B 5/053* (2013.01); *A61B 18/18* (2013.01);
(Continued)

(58) Field of Classification Search
None
See application file for complete search history.

(56) References Cited

U.S. PATENT DOCUMENTS 4,686,127 A    8/1987  Burns et al.
5,044,006 A *  8/1991  Cyrulnik ................ A61N 5/10
                                                         378/113

(Continued)

OTHER PUBLICATIONS

NIH Stem Cell Information Home Page. In Stem Cell Information. Bethesda, MD: National Institutes of Health, U.S. Department of Health and Human Services, 2016 < //stemcells.nih.gov/info/basics/2.htm> (Year: 2016).*

(Continued)

*Primary Examiner* — Yi-Shan Yang
(74) *Attorney, Agent, or Firm* — Fish IP Law, LLP (57) ABSTRACT

A system and method for the present invention requires use of a generator, in combination with a radiation unit, to radiate electromagnetic waveform energy onto a target tissue (i.e. a cellular structure). During radiation of the target tissue in accordance with a predetermined titration-like protocol, the influence of the waveform energy on the cellular structure is periodically monitored. The protocol is stopped when the cellular structure has been transformed or morphed into a desired phenotype.

13 Claims, 4 Drawing Sheets

(51) Int. Cl.
*A61N 1/06* (2006.01)
*A61B 18/18* (2006.01)
*A61B 5/053* (2021.01)
*A61N 7/00* (2006.01)
*A61B 5/00* (2006.01)
A61B 17/00 (2006.01)
A61B 90/00 (2016.01)
A61B 18/00 (2006.01)
A61B 5/055 (2006.01)
A61B 6/03 (2006.01)
A61B 8/08 (2006.01)

(52) U.S. Cl.
CPC .................. *A61N 1/06* (2013.01); *A61N 5/00* (2013.01); *A61N 7/00* (2013.01); *A61B 5/0066* (2013.01); *A61B 5/055* (2013.01); *A61B 6/03* (2013.01); *A61B 8/08* (2013.01); *A61B 2017/00154* (2013.01); *A61B 2017/00194* (2013.01); *A61B 2018/00636* (2013.01); *A61B 2018/00875* (2013.01); *A61B 2090/374* (2016.02); *A61B 2090/378* (2016.02); *A61B 2090/3735* (2016.02); *A61B 2090/3762* (2016.02)

(56) References Cited

U.S. PATENT DOCUMENTS

| | | | |
|---|---|---|---|
| 6,024,690 A | 2/2000 | Lee et al. | |
| 6,033,357 A | 3/2000 | Ciezki et al. | |
| 6,077,213 A | 6/2000 | Ciezki et al. | |
| 6,221,094 B1 | 4/2001 | Bare | |
| 6,309,339 B1 | 10/2001 | Ciezki et al. | |
| 6,521,210 B2 | 2/2003 | Ohkawa | |
| 6,626,816 B1 | 9/2003 | Ciezki et al. | |
| 6,725,081 B2 | 4/2004 | Ciezki et al. | |
| 7,280,874 B2 | 10/2007 | Boehm | |
| 7,418,294 B2 | 8/2008 | May | |
| 7,500,956 B1 | 3/2009 | Wilk | |
| 8,326,408 B2 | 12/2012 | Green et al. | |
| 8,346,559 B2* | 1/2013 | Dean | A61B 5/16 600/301 |
| 8,440,154 B2 | 5/2013 | Fahs, II et al. | |
| 8,591,419 B2 | 11/2013 | Tyler | |
| 9,223,863 B2* | 12/2015 | Dean | A61B 5/16 |
| 9,826,618 B2* | 11/2017 | Eckert | H05H 1/2406 |
| 9,877,892 B2* | 1/2018 | Grant | A61H 23/0236 |
| 10,004,661 B2* | 6/2018 | Grant | A61H 23/0236 |
| 2007/0128590 A1* | 6/2007 | Boehm | C12N 13/00 435/6.12 |
| 2008/0300571 A1* | 12/2008 | LePivert | A61B 18/1492 604/503 |
| 2010/0049261 A1* | 2/2010 | Bare | A61N 1/40 607/1 |
| 2011/0004091 A1* | 1/2011 | Brooks | A61B 5/0093 600/407 |
| 2011/0171188 A1* | 7/2011 | Morfill | A61N 5/00 424/94.1 |
| 2011/0257494 A1* | 10/2011 | Glazier | B82Y 15/00 600/310 |
| 2012/0130287 A1* | 5/2012 | Gruber | A61N 7/00 601/2 |

OTHER PUBLICATIONS

Dubost, G. and Bellossi, A., "Experimental Approach of the Electromagnetic Effects In Vivo Due to the Solitary-Waves Radiated by a Confined Plasma Antenna", Antennas and Propagation, 2007. EuCAP 2007. Date of Conference: Nov. 11-16, 2007. Conference Location: Edinburgh. Publisher: IET.

* cited by examiner

| Class | | | Frequency | Wave length | Energy |
|---|---|---|---|---|---|
| | Y | Gamma rays | 300 EHz | 1 pm | 1.24 MeV |
| | | | 30 EHz | 10 pm | 124 keV |
| | HX | Hard X-rays | | | |
| | | | 3 EHz | 100 pm | 12.4 keV |
| | SX | Soft X-rays | 300 PHz | 1 nm | 1.24 keV |
| | | | 30 PHz | 10 nm | 124 eV |
| | EUV | Extreme ultraviolet | | | |
| | | | 3 PHz | 100 nm | 12.4 eV |
| Visable | NUV | Near ultraviolet | 300 THz | 1 μm | 1.24 eV |
| | NIR | Near Infrared | | | |
| | | | 30 THz | 10 μm | 124 meV |
| | MIR | Mid Infrared | | | |
| | | | 3 THz | 100 μm | 12.4 meV |
| | FIR | Far Infrared | | | |
| | | | 300 GHz | 1mm | 1.24 meV |
| | EHF | Extermely high frequency | | | |
| | | | 30GHz | 1cm | 124 μeV |
| | SHF | Super high frequency | | | |
| | | | 3 GHz | 1 dm | 12.4 μeV |
| | UHF | Ultra high frequency | | | |
| | | | 300 MHz | 1 m | 1.24 μeV |
| | VHF | Very high frequency | | | |
| | | | 30 MHz | 10 m | 124 neV |
| Radio waves | HF | High frequency | | | |
| | | | 3 MHz | 100 m | 12.4 neV |
| | MF | Medium frequency | | | |
| | | | 300 kHz | 1 km | 1.24 neV |
| | LF | Low frequency | | | |
| | | | 30 kHz | 10 km | 124 peV |
| | VLF | Very Low frequency | | | |
| | | | 3 kHz | 100 km | 12.4 peV |
| | VF/ ULF | Voice frequency | | | |
| | | | 300 Hz | 1 Mm | 1.24 peV |
| | SLF | Super Low frequency | | | |
| | | | 30 Hz | 10Mm | 124 feV |
| | ELF | Extremely low frequency | | | |
| | | | 3 Hz | 100 Mm | 124.4 feV |

SYSTEM AND METHOD FOR USING ELECTROMAGNETIC RADIATION TO INFLUENCE CELLULAR STRUCTURES

This application is a continuation-in-part of application Ser. No. 14/488,101, filed Sep. 16, 2014, which is currently pending. The contents of application Ser. No. 14/488,101 are incorporated herein by reference.

FIELD OF THE INVENTION

The present invention pertains generally to systems and methods for causing a transformational or morphological change in a cellular structure using waveform energy radiation. More specifically, the present invention pertains to systems and methods which epigenetically influence cellular structures with waveform energy radiation, wherein the radiation frequency is equal to or near a responsive frequency of the cellular structure being radiated. The present invention is particularly, but not exclusively useful for systems that use electromagnetic waves to alter the resultant functionality of in vivo or in vitro target tissues.

BACKGROUND OF THE INVENTION

It is well known that electromagnetic and sonic waves can have many different effects on tissue; for many different reasons. Moreover, in some cases, the consequences of radiating tissue may be permanent.

Apart from applications where sonic waves may be used to induce or suggest changes in a particular mood or state of mind, it is also recognized that both sonic and electromagnetic waves can also be employed to cause transformative or morphological changes in cellular structure. Not surprisingly, many of these changes may be very beneficial. Thus, within the medical community there is increasing interest insofar as the extent to which such changes may be employed to beneficially alter the functionality of a cellular structure.

With the above in mind, consider the specific case of sonic waves and the effects they can have on tissue cells (i.e. a cellular structure). From a physical perspective, a tissue cell can be likened to a mechanical system. From this perspective it is also to be appreciated that the pressure of a sound wave is the result of the fluctuation (i.e. vibrational) component of the wave in its transmission medium (e.g. air). The importance of these physical observations is that sound (acoustic) pressure acts to exert a force against tissue (mechanical system). And this will happen whenever a sonic wave is incident on the tissue. Thus, the tissue will be influenced by the externally applied forces that are associated with the sound wave. As implied above, this influence will manifest itself on the tissue.

As a mechanical system, each individual cellular structure (tissue cell) has a natural frequency at which it will oscillate if it is not subjected to a continuous or repeated external force (i.e. when it is not damped). Cellular structures, however, are naturally damped. Thus, in response to an externally applied impulse force, amplitudes of the cellular structure's damped vibrational response to this force will progressively diminish. This will be the case unless the cellular structure is somehow otherwise subsequently stimulated, such as when a sustained vibratory frequency is applied to the cellular structure. Most noticeably, there will be no such diminution when the vibratory frequency is at or near the natural frequency of the cellular structure. Instead, in this case, a resonance condition is established wherein the vibratory nature of the cellular structure's response is sustained, and possibly even amplified.

From a biological perspective, each cell type (e.g. a liver cell) will have observable characteristics which naturally result from the cell's environment. A set of these observable characteristics is generally referred to as a phenotype. Further, it is known that the set of characteristics for a defined phenotype of a cellular structure can be epigenetically influenced by externally applied forces. Moreover, this can happen regardless whether the cellular structure is influenced in vivo or in vitro.

As is well known, sonic frequencies are but a small part of the entire electromagnetic spectrum. In particular, sonic frequencies within the electromagnetic spectrum have very low frequencies (e.g. 20-20,000 Hz) with relatively long wavelengths ($f=1/\lambda$). On the other hand, the electromagnetic spectrum extends to x-rays and gamma rays which have very high frequencies (e.g. >300 PHz) with relatively very short wavelengths (e.g. <100 pm). As is also known, electromagnetic radiation of all frequencies will have a physical effect on cellular structures, albeit sometimes negligible. Of particular interest here, however, are the physical effects that result it an identifiable transformative or morphological change in cellular structure. For this purpose, the high frequency radiations are of unique interest insofar as their penetration of the human body is concerned.

In light of the above, it is an object of the present invention to provide a system and method for using a radiation of waveform energy to epigenetically influence tissue cells, to thereby alter the functionality of an in vivo, or an in vitro, target tissue. It is another object of the present invention to provide a system and method for using a radiation of waveform energy to influence a change in target tissue by tuning an electromagnetic wave to a wavelength that is related to the natural frequency of the target tissue. Still another object of the present invention is to provide a system and method for radiating waveform energy, in accordance with a predetermined titration-like protocol, to epigenetically influence tissue cells for the transformation or morphology of the target tissue into a desired phenotype. Yet another object of the present invention is to provide a system and method for using a radiated waveform energy to epigenetically influence tissue cells which is easy to use and commercially cost effective.

SUMMARY OF THE INVENTION

The present invention pertains generally to the transformational or morphological change of cellular tissue under the influence of waveform energy radiation. From an engineering perspective, it is well known that waveform energy radiation creates forces (i.e. exerts pressure) on an object when the radiation is incident on the object. Further, it is also well known that these external forces can cause changes to tissue structure. The present invention is based on this interactive phenomenon.

For purposes of the present invention, the target tissue of interest may be any in vivo or in vitro cellular structure of the human body. It may be an individual cell, or it may be a group of cells together within the intercellular tissue (matrix) that supports the cells. As envisioned for the present invention, target tissue may also be an identifiable structure inside a cell, such as a chromosome. In each case, it is important to appreciate that as a mechanical structure, the cellular structure of a target tissue will have a unique natural frequency.

An initial consideration for implementation of the present invention is the task of defining a desired phenotype for the outcome. For example, the objective of a protocol for the present invention may be the creation of a particular type of stem cell (e.g. liver cell) from an otherwise undefined or undifferentiated cell. In this case, the desired phenotype (outcome) will be defined to have the requisite characteristics of the particular type stem cell that is desired (e.g. liver cell). As another example, the objective of a protocol may be to terminate the viability of a cellular structure, such as by killing cancer cells. Other examples can be cited. In each instance, however, and regardless of the specific outcome that is desired, the present invention employs waveform energy radiation for the purpose of epigenetically influencing a target tissue for its transformation or morphological change into a structure that corresponds to the desired phenotype.

As envisioned for the present invention, the radiation to be employed for influencing target tissue may be of any waveform energy known in the art. It may be electromagnetic radiation in the spectrum between wavelengths of $10^{-25}$ m to $10^3$ m. It may also be periodic mechanical vibrations. In this latter case, the radiation may be acoustic sound waves in the range between 20 Hz and 20 kHz, and may also include infrasound waves (<20 Hz) and ultrasound waves (>20 kHz). Further, the radiation may be either continuous or pulsed, and the tone of the radiation may be either pure (single frequency) or complex (multi-frequency).

Structurally, a system for using a radiation of waveform energy to influence cellular structures within a target tissue will include a combination of various components. These include: components for generating and directing the radiation onto the target tissue; components for monitoring the target tissue; and a computer for controlling the generator and the radiation unit in accordance with a predetermined protocol.

In detail, the generator is used for generating the particular waveform energy radiation that is necessary to influence the target tissue. For this purpose it is important that the radiation be characterized by operational parameters having respective values which are established relative to the natural frequency of the target tissue. At a minimum, these operational parameters will include a frequency f and a volume intensity level v for the radiation, as well as a time duration $t_d$ during which the target tissue is to be radiated. A radiation unit, which is incorporated with the generator, may include optics that are used for directing the radiation electromagnetic radiation (e.g. lasers) onto the target tissue and the cellular structure. Specifically, all of this is done in accordance with a predetermined protocol that is designed to epigenetically influence the target tissue and the cellular structure that may be within the target tissue. In a preferred embodiment of the present invention the radiation unit will be positioned at a distance d from the target tissue. Typically, the distance d will be greater than 10 millimeters (d>10 mm).

As indicated above, control over the system during the conduct of a protocol is managed by a computer. To do this, a device is provided for monitoring a phenotypic response of the target tissue and the cellular structure during the protocol. As envisioned for the present invention, this monitoring function can be performed by an appropriate sensor, or by the periodic performance of a biopsy. In the event, management and control of the protocol by the computer is terminated when the phenotypic response corresponds with the desired phenotype.

A method in accordance with the present invention begins by identifying the target tissue to be influenced (including the cellular structure), and by defining a desired phenotype for the target tissue. A natural frequency for the phenotype can then be determined by reference to the literature. It is then necessary to establish values for the operational parameters (e.g. p, v and $t_d$) that will properly characterize the radiation that is to be used. In particular, it is desirable to establish operational values that are operationally relative to the natural frequency of the target tissue (cellular structure). In detail, with knowledge of this natural frequency, the radiation frequency f can be set to resonate, or partially resonate, with the cellular structure that is to be influenced during conduct of the protocol.

Operationally, once parameters have been established for the radiation, the radiation can be directed onto the target tissue in accordance with a predetermined protocol. As noted above, the purpose here is to epigenetically influence the target tissue and the cellular structure. During the protocol, the target tissue is then monitored in a titration-like process to detect a phenotypic response from the target tissue and the cellular structure. The protocol is terminated when the phenotypic response corresponds with the desired phenotype.

In an embodiment of the present invention the radiation can be pulsed. For this embodiment, each radiation pulse will have a predetermined time duration $t_d$ within a predetermined time interval $t_i$. Specifically, $t_i$ will extend between the successive beginnings of respective radiation pulses (i.e. $t_i > t_d$).

All radiations in the electromagnetic spectrum can be characterized by three physical properties. These properties are unique to the particular radiation and they include: its frequency (f), its wavelength ($\lambda$), and its photon energy (E). Further, it is recognized that electromagnetic radiation interacts with matter in different ways across the spectrum. Based on the way a particular radiation beam interacts with matter, it has been generally classified into a specific region (i.e. class) of the electromagnetic spectrum (e.g. radio, visible, X-rays). Although there are many different regions in the electromagnetic spectrum, and although radiations within each region will generally have similar properties, there are substantial differences between the regions and the transition from one region to another is not well defined.

For purposes of the present invention, the selection of a particular radiation wavelength $\lambda$ from the electromagnetic spectrum for use with the present invention is made with a view toward achieving an identifiable transformative or morphological change in a cellular structure. With this in mind, the selection of an appropriate radiation is accomplished by first identifying and locating the target tissue that is to be radiated. An important consideration here is that the target tissue will most likely be entirely internal tissue. Moreover, it is envisioned that the entire volume of target tissue may need to be radiated.

In accordance with the present invention, the location of target tissue can be accomplished using any of several well-known clinical techniques. For example, imaging techniques such as Optical Coherence Tomography (OCT), Magnetic Resonance Imaging (MRI), Positron Emission Tomography (PET), Computerized Axial Tomography (CAT), or Ultrasound can be employed to accurately locate internal tissues within the human body. Once the target tissue has been located, radiation interaction with the target tissue and other tissue on the radiation beam path must be considered. For this consideration, the selection of operational parameters for the radiation must necessarily depend on the radiation's reaction with the target tissue, and the ability of the radiation to be directed into contact with the target tissue. Most importantly, the selected radiation must be functionally capable of achieving the desired phenotypic response that is required by the radiation protocol.

Beyond using sonic radiations to influence cellular structures, as disclosed elsewhere herein, the present invention also recognizes that radiation from other regions of the electromagnetic spectrum can also be advantageously used for this same purpose. In particular, the present invention recognizes that radiations from other regions of the electromagnetic spectrum may have unique advantages that can be exploited. For instance, radiations such as X-rays and gamma rays are known to have a much greater capability for penetrating through tissue matter than do some of the other regional radiations. Also, shorter wavelength radiations are more energy intensive and tend to be more accurately controlled in focus. As implied above, such characteristics can be advantageously exploited by the present invention.

As used for the present invention, the term "fluence" means the value of radiation energy passing through a given cross-sectional area of the radiation beam during a given time interval. Using this definition, an operational fluence is to be established for the present invention that will affect only a specific, predetermined volume of the target material. The skilled artisan will appreciate that this operational fluence (i.e. photons/unit area) can be altered by the controller, both as to the intensity (i.e. energy level) of the radiation and the extent of its operational effectiveness (i.e. the volumetric size of target tissue to be affected by the radiation). Further, for some applications it is envisioned that the controller may need to be used to move the spatial location of the radiation's operational fluence through the volume of target tissue that is to be radiated.

Structurally, the present invention envisions the use of a source for generating very high frequency, short-wavelength radiation that has favorable tissue penetrating properties. For example, it is known that solitary-waves can be radiated by a confined plasma antenna in a manner which may be useful for purposes of the present invention. More specifically, longitudinal electromagnetic waves (solitary-waves) are known to result from plasma excitation by an electromagnetic radiation. For this purpose, X-ray and gamma ray generators can be considered for use with the present invention. In any case, a tuner is to be used, in combination with the radiation source, to establish and maintain an efficacious wavelength, $\lambda$, for the radiation.

To identify and establish an efficacious $\lambda$, a fundamental frequency for the target tissue needs to be determined. Importantly, this fundamental frequency will be characteristic of the particular phenotype of the desired cellular structure that is to be achieved. Based on the fundamental frequency that is determined, the wavelength $\lambda$ of the radiation that is to be used can then be selected to have a functional relationship with the fundamental frequency. For instance, this relationship can be determined and established by technical considerations, such as by octave evaluation. Preferably, this radiation source will also be used in combination with a controller that will focus the radiation onto target tissue with an operational fluence, and then move the operational fluence over the target tissue, as required.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
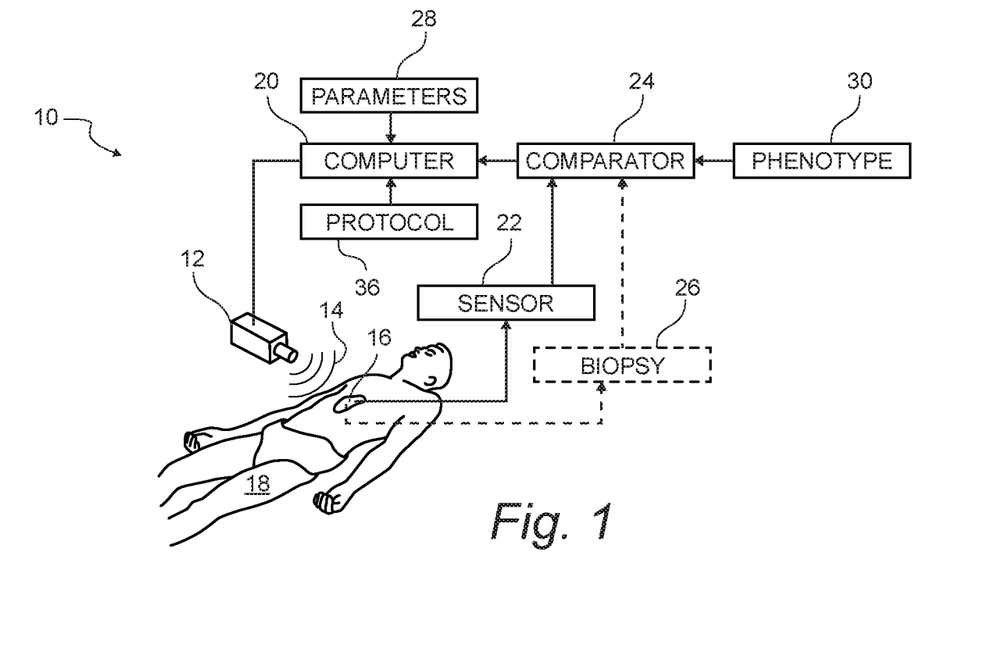
FIG. 1 is a schematic presentation of components for a system in accordance with the present invention.

Referring initially to FIG. 1 a system in accordance with the present invention is shown and is generally designated 10. As shown, the system 10 is to be used for radiating waveform energy to epigenetically influence cellular structures within a target tissue. To do this, the system 10 includes a unit 12 for directing radiation 14 toward a target tissue 16 of a patient 18. In particular, it is envisioned that the unit 12 will be capable of generating a waveform energy radiation 14 that spans the entire electromagnetic spectrum of wavelengths. Further, it is envisioned that the radiation 14 may also include acoustic sound waves in the range between 20 Hz and 20 kHz, as well as infrasound waves (<20 Hz) and ultrasound waves (>20 kHz). In the case of sound waves, the energy waveform of radiation 14 may be either a pure frequency or a complex frequency and, in the case of electromagnetic waves, the radiation 14 may have either a single wavelength $\lambda$, or a combination of different wavelengths. Also, as envisioned for the present invention, the target tissue 16 may be either in vivo as shown in FIG. 1, or it may be in vitro.

Still referring to FIG. 1, it will be seen that the system 10 includes a computer 20 which is connected with the unit 12. Depending on the particular application for system 10, the computer 20 may perform various functions during a same protocol. For instance, in addition to providing operational details for the radiation 14, the computer 20 may also be used to operationally control movements of the unit 12.

As also shown in FIG. 1, the system 10 also includes a sensor 22 which is used to monitor the target tissue 16, and to transfer information pertaining to the target tissue 16 to a comparator 24. For this purpose, the sensor 22 can be of any type well known in the pertinent art that is capable of epigenetically monitoring a transformation or morphology of the target tissue 16. For example, sensor 22 may be employed to perform titration-like methodologies with processes such as bioelectrical impedance analysis and quantitative Polymerase Chain Reaction (PCR) techniques. The results of the monitoring performed by sensor 22 are then provided as input to the comparator 24. In the system 10, the comparator 24 is connected with the computer 20.

For an alternative to the use of a sensor 22 as disclosed above, it will be understood and appreciated by the skilled artisan that an epigenetic change (transformation/morphology) in the target tissue 16 can also be monitored by performing periodic biopsies 26 of the target tissue 16. Again, a titration methodology can be employed. In the event, the particular protocol which is used, its periodicity, and the extent to which the biopsy(ies) 26 is/are employed will be established on a case-by-case basis by the user of the system 10.

In addition to the hardware components for the system 10 mentioned above, various inputs for these components are required for an operation of the system 10. Importantly, the parameters 28 that are required for establishing the waveform energy of radiation 14 are a primary consideration. In particular the parameters 28 will necessarily include a selected frequency f for the vibration of the sound wave in the radiation 14. Also included will be the intensity level v for the max peak amplitudes of the sound wave, and a predetermined time duration $t_d$ for the radiation 14. Depending on the particular application, the time duration $t_d$ for the radiation 14 may be either continuous or pulsed.

Figure 2:
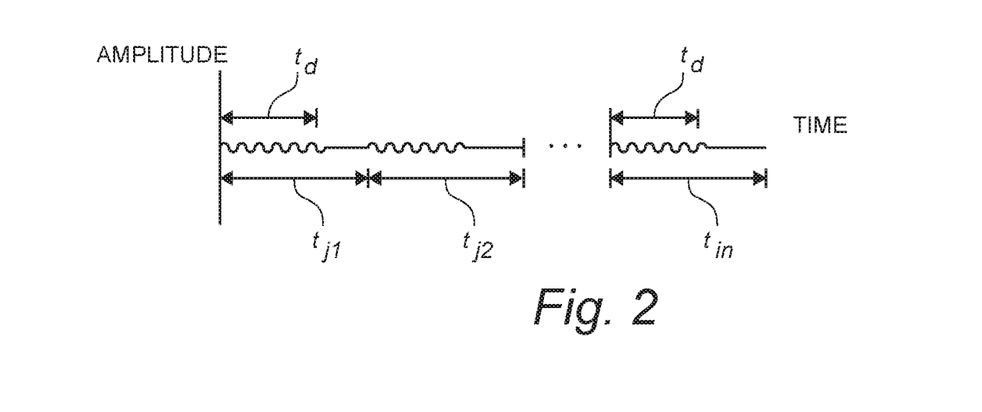
FIG. 2 is a time line of radiation pulses in a representative pulse train of waveform energy radiation in accordance with the present invention.

Referring to FIG. 2, time considerations for the radiation 14 are shown. If the radiation 14 is to be pulsed during an operation of the system 10, each radiation pulse will continue for a predetermined time duration $t_d$ within a predetermined time interval $t_i$. For a train of pulses (e.g. an n number of pulses as shown in FIG. 2), the predetermined time interval $t_i$ for each individual pulse can be established to extend between the successive beginnings of respective radiation pulses in the train (i.e. $t_i > t_d$). Stated differently, each pulse will have a length $t_i$ ($t_i$=time interval), during which the radiation 14 will be generated for the time duration $t_d$. On the other hand, for a continuous radiation 14, $t_d$ will equal $t_i$ (i.e. $t_d = t_i$ and n=1).

Insofar as the frequency f of the radiation 14 is concerned, several considerations are possible. For one, as noted above, the frequency f may be pure or complex. For another, during a radiation 14, the predetermined frequency f may be alternated between a first frequency $f_1$ and a different second frequency $f_2$ (i.e. $f_1 \neq f_2$). Further, alternation of the frequencies may be set to occur at a predetermined repetition rate.

In an operation of the present invention, it is necessary for there to first be a determination and an identification of a desired phenotype 30. By definition, as used for the present invention, a phenotype 30 is set of observable characteristics of an individual resulting from its interaction with the environment. Here, reference to the word "individual" in the definition is taken to mean a cellular structure, a contiguous group of cellular structures, or a portion of a cellular structure, such as a chromosome. For the present invention, the cellular structure is alive and can be either in vivo or in vitro. With this in mind, consider the exemplary cellular structures 32 and 34 shown in FIG. 3.

Figure 3:
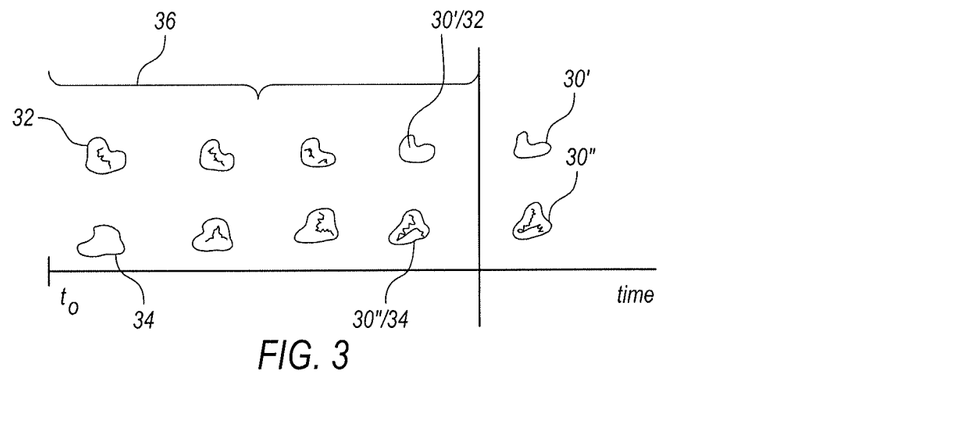
FIG. 3 is an illustration of the sequential progression of epigenetic influence on two different cellular structures during the transformation of the respective cellular structure into a desired phenotype.

For the examples presented here with reference to FIG. 3, consider the cellular structure 32 to be a cancer cell, and the cellular structure 34 to be an undifferentiated cell. The consequence on these respective cellular structures will then depend on the particulars of the protocol 36 that is employed for influencing a particular target tissue 16 with a particular radiation 14. Consider first, the transformation/morphology desired for an active cancer cell (cellular structure) 32. In this instance, the desired phenotype 30' will be a cancer-free cellular structure. Importantly, once the desired phenotype 30' has been identified, and defined, its definitional parameters 28 (including its natural frequency) must be input into the comparator 24. Depending on the characteristics of the desired phenotype 30', operational parameters 28 for the radiation 14 (i.e. f, v, $t_d$, n and $t_i$) are established. Specifics of the particular protocol 36 that are required to influence cellular structure 32 into the desired phenotype 30' are then followed and monitored.

In detail, during the conduct of a protocol 36, the sensor 22 (biopsy 26) is used to observe the cellular structure 32, and the comparator 24 is used to compare the cellular structure 32 with the desired phenotype 30'. Thus, the comparator 24 effectively monitors the transformation/morphology of the cellular structure 32 as it is being influenced by the radiation 14. When the comparator 24 determines a cellular structure 30'/32 has been created which corresponds with the desired phenotype 30' (i.e. a cancer-free cell), the protocol 36 can be terminated.

For another example, consider the transformation/morphology of a cellular structure such as an undifferentiated cell 34. In this case, the desired phenotype 30" may be selected from any of various particular type cells (e.g. a liver cell). As with the earlier example, definitional parameters 28 for a desired phenotype 30" are input into the comparator 24. Also, the required parameters 28 for radiation 14 are established, and an appropriate protocol 36 is followed. As before, when the comparator 24 determines a cellular structure 30"/34 has been created which corresponds with the desired phenotype 30" (i.e. a liver cell), the protocol 36 can be terminated.

Figure 4:
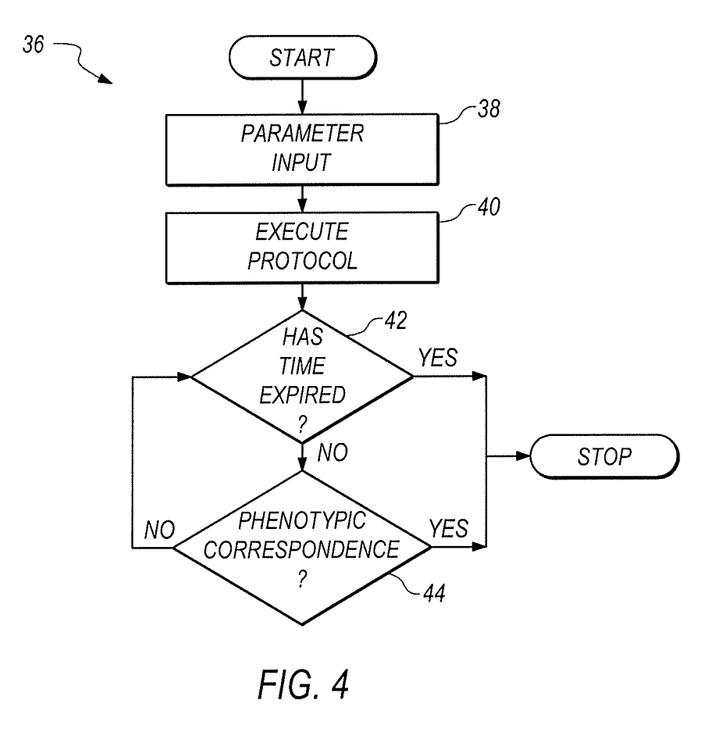
FIG. 4 is a flow chart of the interactive tasks involved in the methodology of the present invention.

For the conduct of a typical protocol 36, refer to FIG. 4. There it will be seen that block 38 requires parameter input for an operation of the system 10. Based on the above disclosure, it will be appreciated that this parameter input is really a two-step process. First, a desired phenotype (e.g. phenotype 30' or 30") needs to be identified and defined. Importantly, this includes selecting a natural frequency for the desired phenotype 30' or 30". Most often this can be accomplished by selecting a natural frequency from previously compiled empirical data. Second, the parameters 28 for operating the radiation unit 12 need to be established (i.e. f, v, $t_d$, n and $t_i$).

Once system 10 has been set for operation as described above, block 40 indicates that the protocol 36 can be performed. The actual conduct of the protocol 36, however, is very event-dependent and may vary considerably depending on the transformation/morphology desired for a particular target tissue 16. Moreover, due to the titration-like methodology that is envisioned by the present invention for a protocol 36, and the many variables that are involved, the actual conduct of a protocol 36 must necessarily be essentially under the purview of the user of the system 10. Accordingly, any time requirements for the protocol 36 that are to be maintained (see inquiry block 42), and a determination of phenotypic correspondence that is indicative of operational completion (see inquiry block 44), are effectively dependent on operational judgments of the user.

Figure 5:
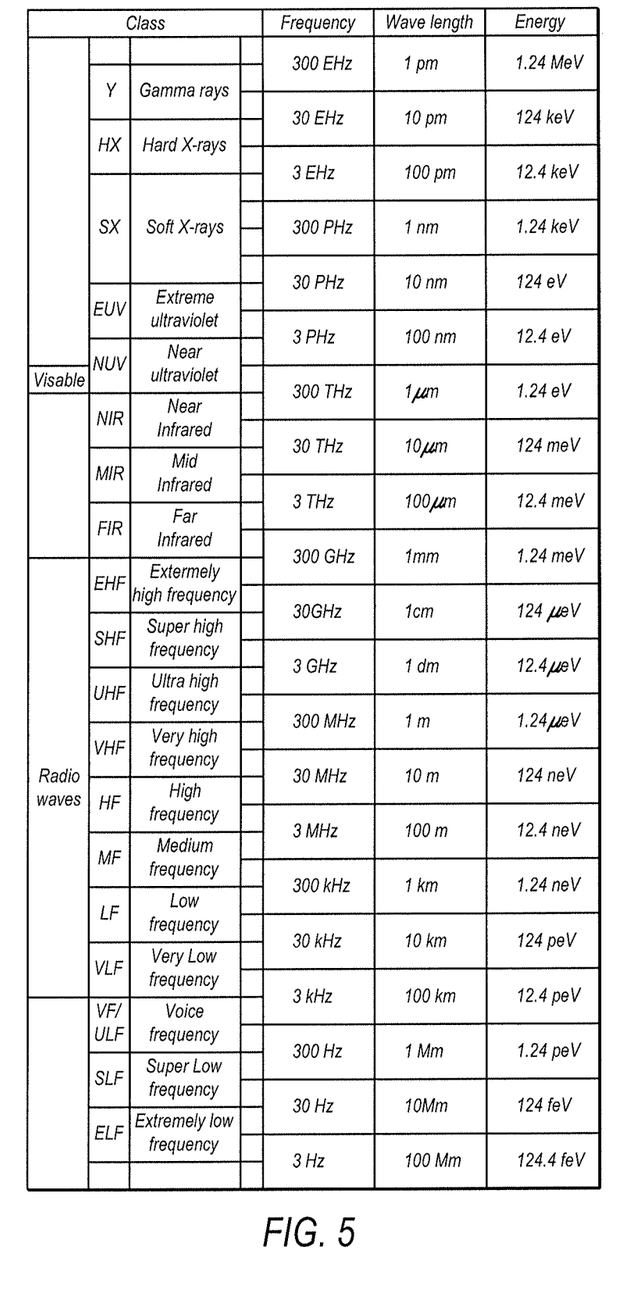
FIG. 5 is a chart of the electromagnetic spectrum.

In another aspect of the present invention, it is to be appreciated that the use of radiation for the purpose of altering cellular structure is envisioned to encompass frequencies and wavelengths that span the entire electromagnetic spectrum. As shown in FIG. 5, the spectrum of electromagnetic radiation is extensive and essentially all-inclusive. It is to be understood, however, that some radiations are easily absorbed by tissue of the patient 18 and, thus, without alteration are not able to penetrate to internal tissue within the body of a patient 18 as may be required. Nevertheless, it is known that longitudinal electromagnetic waves (i.e. solitary-waves) can be useful for achieving deeper penetration toward internal tissue inside the patient 18 than may otherwise be possible. More specifically, confined plasma antennae containing a plasma that is excited by electromagnetic radiation can be useful for this purpose.

Figure 6:
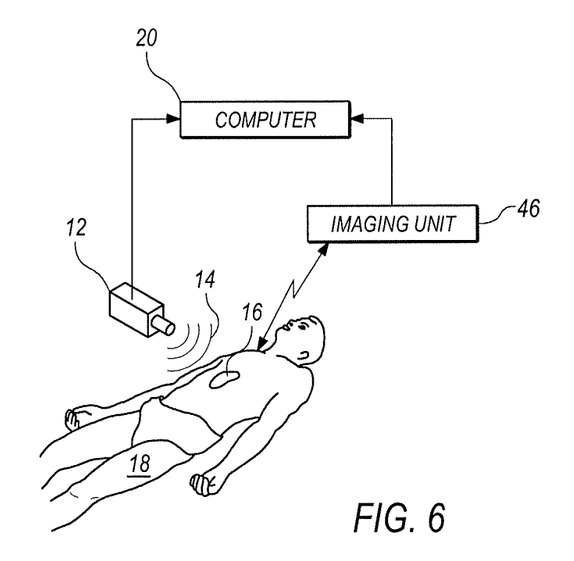
FIG. 6 is a schematic representation of the interactive components incorporated into the system of the present invention for imaging an operational fluence for the present invention.

With the above in mind, and now referring to FIG. 6, it will be seen that an imaging unit 46 may be operationally connected with the computer 20. In this combination, it is envisioned that the imaging unit 46 will create images of internal target tissue 16. Data from these images (not shown) can then be used by a controller in the computer 20 for guiding the radiation 14 from the unit 12 onto the target tissue 16 in accordance with techniques well known in the pertinent art. For the present invention, it is envisioned that the well known imaging techniques to be used may be any of the following: Optical Coherence Tomography (OCT), Magnetic Resonance Imaging (MRI), Positron Emission Tomography (PET), Computerized Axial Tomography (CAT), or Ultrasound.

A methodology for the present invention envisions that the radiation 14 generated by unit 12 will be controlled by the computer 20 to achieve several operational requirements. These include: 1) selecting and generating the particular electromagnetic radiation 14 that is to be used for influencing the target tissue 16; 2) shaping the radiation 14 to establish an operational fluence for the radiation 14 that will be efficacious for the intended purpose; and 3) moving the operational fluence, as needed, through the target tissue 16.

Insofar as the term operational fluence has been used for this disclosure, the term "operational fluence" is defined to mean the photon energy in a radiation 14, per unit cross-sectional area, measured perpendicular to the direction of propagation of the radiation 14. It is to be appreciated that the net result of this operational influence may actually affect a volume of tissue. In each case, it will be appreciated that the operational fluence is established with both the characteristics of the target tissue 16, and the desired phenotypic result in mind.

As indicated above, the present invention envisions moving the operational fluence of the radiation 14 over the target tissue 16. For this purpose, a controller in the computer 20 may be used to direct the operational fluence under the control of the unit 12. As also indicated above, the wavelength $\lambda$ of the radiation 14 needs to have a functional relationship with the fundamental frequency of the cellular structure 34 that is being influenced. In particular, this fundamental frequency is most likely the natural frequency of the cellular structure 34. For any of several different reasons, however, the fundamental frequency may be slightly different from the natural frequency of the cellular structure 34. In any event, the wavelength $\lambda$ that is used by the system 10 for influencing the cellular structure 34 must have a relationship with the fundamental frequency of the cellular structure 34. By definition, $f=1/\lambda$. Further, an octave is defined $f_{high}-2f_{low}=0$. Thus, using these relationships, an efficacious frequency for use with the present invention can be translated into an operational wavelength $\lambda$ for the electromagnetic radiation 14. With this in mind, the present invention envisions using the higher wavelength radiations from the electromagnetic spectrum (FIG. 5) for their operational capabilities (e.g. tissue penetration ability).

While the particular System and Method for Electromagnetic Radiation for Influencing Cellular Structures as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method to epigenetically influence a cancerous cell in a target tissue comprising:
   determining a resonant frequency of the cancerous cell;
   defining a desired phenotype for the cancerous cell;
   generating waveform energy at an octave of the resonant frequency;
   directing the waveform energy onto the target tissue to epigenetically influence the cancerous cell; and
   using a sensor to monitor a phenotypic response of the cancerous cell to the waveform energy to determine whether the cancerous cell has produced the desired phenotype;
   wherein the sensor is configured to monitor the phenotypic response of the cancerous cell via a bioelectrical impedance analysis, and
   wherein the desired phenotype is a cancer-free cellular structure.

2. The method as recited in claim 1 further comprising:
   tuning the waveform energy to select a wavelength $\lambda$ that corresponds to the octave of the resonant frequency;
   adjusting a peak value of amplitudes of the waveform energy to a selected intensity level v;
   providing a predetermined time duration $t_d$ for activation of the generating step; and
   selectively moving an operational fluence along a predefined pathway through the target tissue.

3. The method as recited in claim 2, wherein the waveform energy is continuous during the predetermined duration $t_d$.

4. The method as recited in claim 2 wherein the tuning step is accomplished by selecting the wavelength $\lambda$ of the waveform energy for transit through tissue surrounding the target tissue, to the target tissue at a penetration depth.

5. The method as recited in claim 2 wherein the waveform energy is pulsed during the generating step, with each waveform energy pulse having radiation of the predetermined time duration $t_d$ within a predetermined time interval $t_i$ between successive beginnings of respective waveform energy pulses.

6. The method as recited in claim 1 wherein the generating step further comprises exciting a plasma with the waveform energy in the form of electromagnetic radiation to create a longitudinal electromagnetic wave, wherein the plasma is confined in a plasma antenna.

7. The method as recited in claim 1 further comprising a step of imaging the target tissue to create images of the target tissue for use during the directing step.

8. The method as recited in claim 7 wherein the imaging step is accomplished using a technique selected from a group consisting of Optical Coherence Tomography (OCT), Magnetic Resonance Imaging (MRI), Positron Emission Tomography (PET), Computerized Axial Tomography (CAT), or Ultrasound.

9. The method as recited in claim 7 wherein the waveform energy is at least one of an X-ray and a gamma ray.

10. A method for epigenetically influencing a cancerous cellular structure in a target tissue comprising steps of:
    defining a desired phenotype for the cancerous cellular structure in the target tissue, wherein the cancerous cellular structure has a fundamental frequency, and the desired phenotype is a cancer-free cellular structure;

radiating the target tissue with waveform energy at the fundamental frequency via a predetermined protocol to result in a phenotypic response of the cancerous cellular structure;

monitoring the phenotypic response of the cancerous cellular structure in the target tissue by a sensor via a bioelectrical impedance analysis; and terminating the predetermined protocol when the phenotypic response corresponds with the desired phenotype.

11. The method as recited in claim 10 wherein the predetermined protocol further comprises:

tuning the radiation to a wavelength $\lambda$ that corresponds to the fundamental frequency;

adjusting a peak value of amplitudes of the radiation to a volume intensity level v; and providing the time duration $t_d$ for activation of the generating step.

12. The method as recited in claim 10 wherein the waveform energy is electromagnetic radiation having a functional relationship with the fundamental frequency, and wherein the electromagnetic radiation is established by an octave evaluation.

13. The method as recited in claim 10, wherein the target tissue is selected from a group consisting of in vivo tissue and in vitro tissue.

* * * * *

UNITED STATES PATENT AND TRADEMARK OFFICE
CERTIFICATE OF CORRECTION

PATENT NO. : 11,118,172 B2
APPLICATION NO. : 14/632941
DATED : September 14, 2021
INVENTOR(S) : Grant et al.

It is certified that error appears in the above-identified patent and that said Letters Patent is hereby corrected as shown below:

In the Claims

Column 10, Line 34, "during the predetermined duration" should read --during the predetermined time duration--

Signed and Sealed this
Nineteenth Day of July, 2022

Katherine Kelly Vidal
*Director of the United States Patent and Trademark Office*